United States Patent [19]

Mayer et al.

[11] Patent Number: 6,054,141

[45] Date of Patent: Apr. 25, 2000

[54] SEX PHEROMONE SYNERGIST

[75] Inventors: Marion S. Mayer; Robert E. Doolittle; Everett R. Mitchell, all of Gainesville, Fla.

[73] Assignee: The United States of America as represented by the Secretary of Agriculture, Washington, D.C.

[21] Appl. No.: 09/258,304

[22] Filed: Feb. 26, 1999

[51] Int. Cl.[7] .................................................. A01N 25/02
[52] U.S. Cl. .......................... 424/405; 424/406; 424/409; 424/410; 424/84; 574/703; 574/693
[58] Field of Search .................................. 574/703, 693; 568/420, 448, 459, 476; 424/405, 406, 409, 410, 84

[56] References Cited

U.S. PATENT DOCUMENTS

| | | | |
|---|---|---|---|
| 3,009,960 | 11/1961 | Shoots et al. | 568/476 |
| 5,344,821 | 9/1994 | Kingan et al. | 514/12 |
| 5,665,344 | 9/1997 | Pair et al. | 424/84 |

OTHER PUBLICATIONS

Burger et al.; Tetrahedron Letters, vol. 31, No. 40, pp. 5771–5772, 1990.
Light et al.;Chemoecology 4:145–152, 1993.
Carpenter et al.; J. Georgia Entomol. Soc., vol. 17, pp. 87–93 (1982).
Grant et al.; Journal of Chemical Ecology, vol. 15, No. 12, pp. 2625–2634, 1989.
Mayer et al.; Journal of Chemical Ecology, vol. 21, No. 11, pp. 1875–1891, 1995.

*Primary Examiner*—Neil S. Levy
*Attorney, Agent, or Firm*—M. Howard Silverstein; John D. Fado; G. Byron Stover

[57] ABSTRACT

Disclosed is the compound 6-vinyldecanal and its use as a sex pheromone synergist. The invention also includes a composition of matter, comprising 6-vinyldecanal and an agriculturally acceptable carrier. The invention further includes a composition suitable for attracting insects, comprising 6-vinyldecanal and an insect sex pheromone, as well as traps containing such a composition.

22 Claims, No Drawings

SEX PHEROMONE SYNERGIST

BACKGROUND OF THE INVENTION

This invention relates to the use of the compound 6-vinyldecanal as a sex pheromone synergist.

DESCRIPTION OF THE RELATED ART

Insect infestation of crops is a primary cause of crop loss throughout the United States. A wide variety of chemical pesticides has been relied upon in the past to control insect pests. However, environmental concerns as well as consumer safety concerns have led to the deregistration of many pesticides and a reluctance to use others on agricultural products which are ultimately consumed as food. As a consequence, scientists have lately pursued the development of alternative biological control agents which are environmentally safer.

The corn earworm *Helicoverpa zea* (*H. zea*), a noctuid Lepidoptera moth, causes an estimated $1.2 billion in crop damages each year. Therefore, scientists have been exploring biocontrol methods which are effective for this insect.

A number of past studies have focused on the use of natural sex attractants of insects, or synthesized analogs thereof, for the purpose of disrupting reproductive behavior.

Sekul et al. (*J. Econ. Entomol.* 68: 603–604, 1975) identified Z-11-hexadecenal, produced and released by the adult female of *H. zea*, and referred to the compound as a sex attractant inhibitor. The compound elicited strong sex stimulation in caged males; however, in field experiments, the catch of males in sticky or electric grid traps was inhibited in the presence of the compound.

Mitchell et al. (U.S. Pat. No. 4,083,995) disclosed a chemical of non-biological origin, (Z)-9-tetradecen-1-ol formate, which was effective in reducing mating in corn earworm and tobacco budworm moths.

Burger et al. (*Tetrahed. Letters* 31: 5771–5772, 1990) disclosed that 7-vinyldecyl acetate, a by-product of the synthesis of the natural sex attractant (E)-8-dodecenyl acetate, acted as a strong pheromonal inhibitor in the false codling moth.

Other studies (see, for example, Raina et al., U.S. Pat. Nos. 5,032,567; Kingan et al., *Soc. Neurosci. Abst.* 17: 549, 1991; Fraser et al., 5,041,379; Kingan et al., 5,344,821) focused on the use of peptides as reproduction inhibitors.

A different strategy focused on the use of natural sex attractants, alone or combined with synergistic compounds, to increase trap captures of insects.

Light et al. (*Chemoecol.* 4: 145–152, 1993) disclosed that the capture of adult male *H. zea* and codling moth insects in female sex pheromone traps was enhanced or synergized by a certain group of host plant volatiles, the so-called greenleaf volatiles (GLVs), which are simple aliphatic six-carbon primary alcohols, aldehydes and acetates found ubiquitously throughout the plant kingdom. Sex pheromone traps containing one of the prominent GLVs from certain *H. zea* hosts, (Z)-3-hexenyl acetate, not only significantly increased the capture of *H. zea* males, but were preferred over traps baited only with sex pheromone.

Pair et al. (U.S. Pat. No. 5,665,344) disclosed that compositions of cis-jasmone, a volatile constituent of the Japanese honeysuckle flower, used alone or in combination with other Japanese honeysuckle flower volatiles, particularly linalool and/or phenylacetaldehyde, was effective in attracting adult Lepidoptera.

Mayer et al. (*J. Chem. Ecol.* 21: 1875–1891, 1995), disclosed that 6-vinyldecyl acetate and 10-vinyltetradecyl acetate each synergistically improved the attraction to the sex attractant (Z)-7-dodecenyl acetate in the cabbage looper (*Trichoplusia ni*).

SUMMARY OF THE INVENTION

The present invention is directed to the use of the compound 6-vinyldecanal as a sex pheromone synergist. Specifically, the invention in its broadest sense includes the compound 6-vinyldecanal itself. The invention also includes a composition of matter, comprising 6-vinyldecanal and an agriculturally acceptable carrier. The invention further includes a composition suitable for attracting insects, comprising 6-vinyldecanal and an insect sex pheromone.

DESCRIPTION OF THE PREFERRED EMBODIMENTS

According to the invention, there is provided a compound, 6-vinyldecanal, and compositions of matter containing this compound which are useful as sex pheromone synergists for attracting male insects, preferably insects of the order Lepidoptera.

A composition of matter in accordance with the invention comprises 6-vinyldecanal and an inert liquid carrier. Suitable inert liquids are well known to those of skill in the art and include but are not limited to alcohols, ethers, glycols, ketones and esters. The composition may be applied to a solid substrate. Suitable substrates may comprise a non-porous material, such as rubber, or a porous material, such as paper. Other non-limiting examples include clays, celluloses or synthetic polymers. A suitable substrate can be determined by those of skill in the art, taking into account the specific conditions in which the invention is to be used.

The choice of a particular substrate is not preferred, however, it is preferred that the substrate be porous in order to control the volatility of the 6-vinyldecanal solution. The inventors have found that the use of a non-porous substrate tends to lead to greater volatility of the 6-vinyldecanal solution, as compared to the use of a porous substrate.

Another composition of matter in accordance with the invention is a composition suitable for attracting insects, comprising 6-vinyldecanal and an insect sex pheromone. The composition is synergistically more effective in attracting insects than the insect sex pheromone alone. The 6-vinyldecanal and the insect sex pheromone may be physically combined in solution and applied together to a solid substrate. It is also possible to apply the two substances separately in close proximity, with one substrate or a portion thereof containing thereon or therein the 6-vinyldecanal and another substrate (or another portion of the same substrate) containing thereon or therein the insect sex pheromone. In this way, the composition of the invention is actually formed as a vapor upon the simultaneous volatilization of the two main components.

Preferably, the insect sex pheromone used in accordance with the invention is naturally found in adult Lepidoptera females. Lepidopteran pheromones suitable for use herein are generally well known in the art. Overviews of the pheromones for many insects, including many Lepidoptera, have been described and include, for example, Mayer and McLaughlin, *Handbook of Insect Pheromones and Sex Attractants*, CRC Press, 1991; and Tamaki, *Sex Pheromones* in *Comprehensive Insect Physiology, Biochemistry and Pharmacology*, vol. 9 "Behavior", Kerkut and Gilbert (Eds.), Pergamon Press, pp. 145–179.

It is even more preferred that the insect sex pheromone is found in species from the genus Helicoverpa, Heliothis or Plutella. It is most preferred that the insect sex pheromone is found in *Helicoverpa zea, Heliothis punctigera, Heliothis armigera* or *Plutella xylostella*. The insect sex pheromone may be extracted from the insect, or it may be produced synthetically or semi-synthetically.

In one embodiment of the invention, the insect sex pheromone comprises at least one member selected from the group consisting of (Z)-11 hexadecenal, (Z)-9-hexadecenal, (Z)-7-hexadecenal and hexadecenal. It is preferred that the insect pheromone comprises at least two of the above listed pheromones. It is most preferred that the insect sex pheromone comprises (Z)-11 hexadecenal and Z-9-hexadecenal.

The amount of synergist which is used in combination with insect sex pheromone is selected to provide a synergistically-effective attraction of the insects. A "synergistically-effective amount" means that quantity of a combination of synergist and insect sex pheromone that attracts the target insects to a location of a bait at a rate statistically significantly higher than the attraction to a location baited with the insect sex pheromone only. Effective airborn concentrations of the synergist may vary with the particular target insect, its population density, the size of the area to be treated, environmental conditions such as temperature, humidity and wind conditions, and the type of vehicle or carrier employed, as well as the amount of insect sex pheromone used. Typically, the amount of synergist used would be between 10 nanograms and 1000 micrograms per trap. However, a skilled artisan can determine the effective concentration of synergist necessary for his or her particular purposes, without undue experimentation.

The synergist and composition containing the same may be used in a number of ways, including monitoring or controlling insect populations. In one preferred embodiment, the compositions of the invention may be placed within traps to monitor population changes. Precise monitoring enables growers to reduce the number of insecticide applications when populations are low. In other preferred embodiments, the compositions of the invention may be used to control insect populations by employing large numbers of traps, or by combinations with an effective amount of an insect toxicant or pesticide to kill adult insects. Suitable toxicants for use herein may be readily selected by a worker of skill in the art, and include but are not limited to organophosphate, carbamate, nitroguanidine and synthetic pyrethroid insecticides.

Thus, the present invention also includes an insect trap, containing 6-vinyldecanal, an insect sex pheromone, and trapping means for trapping the insect. The trap may also include an effective amount of an insecticide to kill the trapped insect.

In addition, the present invention includes improvements in methods of trapping male insects. In a standard method of trapping male insects comprising baiting a trap, having trapping means for trapping the male insects, with an insect sex pheromone to lure the male insects to the trap and trapping the male insects via the trapping means, an improvement in accordance with the invention comprises farther baiting the trap with a sex pheromone synergist comprising 6-vinyldecanal.

It is envisioned that the synergist of the invention, and compositions containing the same, may be used in conjunction with any type of appropriate trap or attractant disseminator as known in the art. The synergist or composition containing the same may be applied or disseminated using a variety of conventional techniques, such as in an exposed solution, impregnated into a wicking material or other substrate, or incorporated in a dispenser. Further, the components of the composition of the invention may be combined in a single dispenser provided within a single trap, or provided separately in a plurality of dispensers, all within a single trap. The compound or compositions of the invention may be applied to a trap undiluted, or formulated in an inert carrier. Volatilization may be controlled or retarded by inclusion of an extender, such as mineral oil. Controlled release over an extended period of time may also be effected by placement of the compound or compositions of the invention within vials, within a permeable septum or cap, by encapsulation using conventional techniques, or absorption into a porous substrate.

The following examples are intended only to further illustrate the invention and are not intended to limit the scope of the invention in any way.

EXAMPLE 1

Chemical Synthesis

2-Butyl-7-(tert-butyldimethylsilyloxy)-1-heptanol

To a solution of diisopropylamine (16.8 ml, 120 mmol) in anhydrous tetrahydrofuran (THF) (125 ml) held at −30 to −40° C., n-butyllithium (120 mmol, 50 ml of a 2.4 M solution in hexanes) was added dropwise. The resulting solution was stirred for 15 min and hexanoic acid (6.97 g, 60 mmol) in a little THF was added dropwise keeping the temperature below 0° C. The milky white suspension was stirred at 0° C. for 10 min and 1,3-dimethyl-3,4,5,6-tetrahydro-2(1H)pyrimidinone (DMPU) (9.5 ml, 78 mmol, 1.2 to 1.3x the amount of hexanoic acid on a molar basis) was added and the mixture allowed to come to room temperature (22° C.) over one hour. The solution was chilled to 0° C. and 1-bromo-5-(tert-butyldimethylsilyloxy)pentane (14.35 g, 60 mmol) was added. After stirring at room temperature for 12 h, the reaction was quenched by addition of 100 ml of a saturated solution of $KHSO_4$ (100 ml). The organic layer was diluted with ethyl ether (250 ml) and washed with a solution of saturated sodium chloride (brine) (4×100 ml), dried over anhydrous $MgSO_4$. The drying agent was removed by filtration and the solvent removed by evaporation yielding a red oil (15 g). This oil was dissolved in anhydrous ethyl ether (50 ml) and added to a suspension of lithium tetrahydroaluminate (LTHA) (4.55 g, 120 mmol) in 125 ml of anhydrous ether. The reaction mixture was heated under reflux for 8 h, chilled and decomposed with 10% NaOH (100 ml). The mixture was extracted with ether (3×100 ml) and the combined extracts washed with water and dried over anhydrous $K_2CO_3$. Removal of the solvent in vacuo and purification of the residual oil by preparative medium-pressure liquid chromatography (PMPLC) on Merck 60 silica gel (0.040–0.063 mm) yielded 12.03 g (69%) of 2-butyl-7-(tert-butyldimethylsilyloxy )-1-heptanol.

$^1$H NMR spectrum: 0.05 s, 6H ($CH_3$); 0.87 s, 9H ($CH_3$); 0.88 t, 3H, J=7.1 ($CH_3$); 1.12–1.34 m, 12H ($CH_2$); 1.47 m, 1H (CH); 1.46 m, 2H ($CH_2$); 3.48 d, 2H, J=5.4 ($CH_2$); 3.54 t, 2H, J=6.6 ($CH_2$). For $C_{17}H_{38}O_2Si$ (302.6) calculated: 67.48% C, 12.66% H; found: 67.39% C, 12.78% H.

2-Butyl-7-(tert-butyldimethylsilyloxy)heptanal

A solution of 2-butyl-7-(tert-butyldimethylsilyloxy)-1-heptanol in dichloromethane (10 ml) was added to a suspension of pyridinium chlorochromate (8.09 g, 38 mmol) and sodium acetate (150 mg) in 30 ml of dichloromethane and stirred at ambient temperature for several hours. After the usual work up followed by PMPLC, 6.61 g (88%) of 2-butyl-7-(tert-butyldimethylsilyloxy)heptanal was obtained.

¹H NMR spectrum: 0.05 s, 6H (CH₃); 0.88 s, 9H(CH₃); 0.88 t, 3H, J=7.2 (CH₃); 1.23–1.62 m, 14H (CH₂ and CH); 1H (CH); 2.36 m; 3.57 t, J=6.7 (CH₂); 9.53 d, 1H, J=3.1 (CHO). For $C_{17}H_{36}O_2Si$ (300.6) calculated: 67.94% C, 12.07% H; found: 68.01% C, 12.15% H.

8-(tert-Butyldimethylsilyloxy)3-butyloct-1-ene

2-Butyl-7-(tert-butyldimethylsilyloxy)heptanal (6.01 g, 20 mmol) in 15 ml of anhydrous THF was added dropwise to a freshly prepared solution of methylidene(triphenyl) phosphorane (22 mmol in 125 ml of anhydrous THF/hexane at 0° C. over a period of 15 min. The mixture was warmed to room temperature, stirred for 8 h, and poured into 300 ml of ice/water and extracted (3×75 ml) with ether. The combined organic extracts were washed with water and dried over anhydrous $MgSO_4$. Solvents were removed by evaporation and pentane (250 ml) was added to the red oily residue. The mixture was chilled to 0° C. and the precipitated $Ph_3PO$ removed by filtration The precipitate was washed with ice-cold pentane and the filtrate concentrated in vacuo. The crude product was purified by PMPLC yielding 4.06 g (68%) of 8-(tert-butyldimethylsilyloxy)-3-butyloct-1-ene.

¹H NMR spectrum: 0.05 s, 6H (CH₃); 0.88 t, 3H, J=7.1 (CH₃); 0.88 s, 9H (CH₃); 1.18–1.60 m, 14H (CH₂); 2.18 m, 1H (CH); 3.59 t, 2H, J=6.6 (CH₂); 4.92–4.94 m, 2H (CH=CH2); 5.52 ddd, J=8.8, 10.2, 16.8 (CH=). For $C_{18}H_{38}OSi$ (298.58) calculated: 72.41% C, 12.83% H; found: 72.33% C, 12.90% H.

6-Butyloct-7-en-1-ol 8-(tert-butyldimethylsilyloxy)-3-butyloct-1-ene (4.0 g, 13.4 mmol) was added to a solution of tetrabutylammonium fluoride (1 M, 14 ml) in THF, and the mixture was stirred at ambient temperature for 24 h. Standard work-up followed by PMPLC yielded 2.05 g (83%) of 6-butyl-7-en-1-ol.

¹H NMR spectrum: 0.87 t, 3H, J=7.2 (CH₃); 1.20–1.59 m, 14H (CH₂); 2.20 m, 1 H (CH); 3.64 t, 2H, J=6.6 (CH₂); 4.91–4.94 m, 2H (=CH₂); 5.52 ddd, 1 H, J=8.8, 10.8, 16.4 (CH=). For $C_{12}H_{24}O$ (180.32) calculated: 78.20% C, 13.13% H; found: 78.34% C 13.25% H.

6-Butyloct-7-en-1-yl acetate

6- Butyloct-7-en-1-ol (800 mg, 4.34 mmol) was converted to the acetate in a standard procedure with acetic anhydride, pyridine and 4-dimethylaminopyridine (DMAP). Subsequent purification by PMLPC yielded 914 mg (93%) of 6-butyloct-7-en-1-yl acetate.

¹H NMR spectrum: 0.88 t, 3H, J=7.1 (CH₃); 1.11–1.57 m, 14H (CH₂); 2.05 s, 3H (OCOCH₃); 2.18 m, 1H (CH); 3.66 t, 2H, J=6.6 (CH₂); 4.93–4.94 m, 2H (=CH₂); 5.56 ddd, IH, J=8.8, 10.6, 16.7 (CH=). For $C_{14}H_{26}O_2$ (226.35) calculated: 74.29% C, 11.57% H; found: 74.43% C, 11.70% H.

6-Butyloct-7-enaldehyde (aka 6-vinyldecanal)

A dichloromethane (1 ml) solution of 6-butyloct-7-en-1-ol (400 mg, 2.17 mmol ) was oxidized with a suspension of pyridinium chlorochromate (0.65 g, 3 mmol) and sodium acetate (20 mg) in 2 ml of dichloromethane. Standard work-up followed by PMLPC yielded 288 mg (70%) of 6-butyloct-7-enaldehyde.

¹H NMR spectrum: 0.89 t, 3H, J=7.1 (CH₃); 1.05–1.51 m, 12H (CH₂); 2.24 m, 1H (CHO; 3.29 m, 2H (CH₂); 4.92–4.94 m, 2H (=CH₂); 5.49 ddd, 1H, J=8.7, 10.3, 16.8 (CH=); 9.66 t, 1H, J=3.0 (CHO). For $C_{12}H_{22}O$ (182.3) calculated: 79.06% C, 12.16% H; found: 78.95% C, 12,27% H.

EXAMPLE 2

Field Trap Assays

Texas Pheromone cone traps were deployed in cotton fields near Alachua, Fla., during late summer 1997 and baited with commercially prepared Hercon, plastic bi-layered orange wafers that were charged with a total of 1.25 mg of four compounds: (Z)-7-hexadecenal 2%; (Z)-9-hexadecenal, 3%; (Z)-11-hexadecenal, 87%; and, hexadecenal, 8%. Either 0, 6.23 or 62.3 micrograms of the synergist were pipetted onto 1 inch×1 inch Whatman #1 filter papers and placed next to the plastic lure. The experimental design of the definitive trap assay consisted of 6 rows of traps each having 2 groups of 3 locations. The traps were baited with the synergist each evening at dusk and the numbers of males captured were counted the following morning. Each assay group was run over 6 nights. The entire assay comprised 72 replications of each synergist dosage. The data were analyzed by split-plot Analysis of Variance (ANOVA) with blocks and lures as the main plot source of variation and locations as "subplot" treatment. Individual means were tested by Duncan's test and multiple means were compared by contrast statements within the analysis (SAS, PROC GLM).

As a result of the test, two groups of traps provide definitive evidence that: (1) the synergist significantly enhanced trap captures (assay series 1 and 6); (2) the synergist probably lost effectiveness as expected when dispensed from rubber septa (assay series 1); (3) the response to the synergist was dose-related (assay series 6); and (4) the effect of the synergist was most pronounced when field populations were low (assay series 6).

TABLE 1

Results of two groups of assays of synergist

| Assay Group 1 | |
|---|---|
| Synergist Treatment | Numbers of Males Captured[1] |
| Wafer + Synergist(Septum)[2] | 6.6 b |
| Wafer + Synergist (Paper)[2] | 23.0 a |
| Wafer | 8.0 b |

| Assay Group 2 | |
|---|---|
| Synergist Dose (micrograms) | Numbers of Males Captured |
| 0 | 0.3 a |
| 6.3 | 0.6 a |
| 63.2 | 1.1 b |

[1]Means in a column followed by the same letter are not significantly different (P > 0.05); Duncan's test.
[2]Dose of Synergist is 200 µg of 6-vinyldecanal.

We claim:

1. In a method of trapping male insects comprising baiting a trap, having trapping means for trapping the male insects, with an insect sex pheromone to lure the male insects to the trap and trapping the male insects via the trapping means, the improvement comprising further baiting the trap with a sex pheromone synergist comprising 6-vinyldecanal.

2. The method of claim 1, wherein the male insects are Lepidoptera.

3. The method of claim 1, wherein the male insects are from the genus Helicoverpa, Heliothis or Plutella.

4. A composition comprising 6-vinyldecanal and an insect sex pheromone.

5. The composition of claim 4, wherein the composition is a vapor.

6. The composition of claim 4, wherein the insect sex pheromone comprises at least one member selected from the group consisting of (Z)-11 hexadecenal, (Z)-9-hexadecenal, (Z)-7-hexadecenal, hexadecenal, and mixtures thereof.

7. The composition of claim 4, wherein the insect sex pheromone comprises (Z)-11 hexadecenal.

8. The composition of claim 4, wherein the insect sex pheromone is extracted from adult Lepidoptera females.

9. The composition of claim 8, wherein the insect sex pheromone is extracted from species from the genus Helicoverpa, Heliothis or Plutella.

10. The composition of claim 9, wherein the insect sex pheromone extracted from in *Helicoverpa zea, Heliothis punctigera, Heliothis armigera* or *Plutella xylostella*.

11. An insect trap, comprising 6-vinyldecanal, an insect sex pheromone and trapping means for trapping the insect.

12. The insect trap of claim 11, wherein the insect sex pheromone comprises at least one member selected from the group consisting of (Z)-11 hexadecenal, (Z)-9-hexadecenal, (Z)-7-hexadecenal, hexadecenal and mixtures thereof.

13. The insect trap of claim 11, wherein the insect sex pheromone comprises (Z)-11 hexadecenal.

14. The insect trap of claim 11, wherein the insect sex pheromone is extracted from adult Lepidoptera females.

15. The insect trap of claim 11, wherein the insect sex pheromone is extracted from species from the genus Helicoverpa, Heliothis or Plutella.

16. The insect trap of claim 11, wherein the insect sex pheromone is found extracted from *Helicoverpa zea, Heliothis punctigera, Heliothis armigera* or *Plutella xylostella*.

17. The insect trap of claim 11, further comprising an effective amount of an insecticide to kill the trapped insect.

18. The insect trap of claim 11, wherein the insect sex pheromone comprises at least two members selected from the group consisting of(Z)-11-hexadecenal, (Z)-9-hexadecenal, (Z)-7-hexadecenal, and hexadecenal.

19. The insect trap of claim 11, wherein the insect sex pheromone comprises (Z)-11-hexadecenal and (Z)-9-hexadecenal.

20. The method of claim 1, wherein the male insects are from the species *Helicoverpa zea, Heliothis punctigera, Heliothis armigera* or *Plutella xylostella*.

21. The composition of claim 4, wherein the insect sex pheromone comprises at least two members selected from the group consisting of (Z)-11-hexadecenal, (Z)-9-hexadecenal, (Z)-7-hexadecenal, and hexadecenal.

22. The composition of claim 4, wherein the insect sex pheromone comprises (Z)-11-hexadecenal and (Z)-9-hexadecenal.

* * * * *